US009883696B2

(12) United States Patent
Liu

(10) Patent No.: US 9,883,696 B2
(45) Date of Patent: Feb. 6, 2018

(54) BATTERY ROD ASSEMBLY AND ELECTRONIC CIGARETTE

(71) Applicant: Kimree Hi-Tech Inc., Tortola, Virgin Islands (GB)

(72) Inventor: Qiuming Liu, Guangdong (CN)

(73) Assignee: HUIZHOU KIMREE TECHNOLOGY CO., LTD SHENZHEN BRANCH, Guangdong (CN)

( * ) Notice: Subject to any disclaimer, the term of this patent is extended or adjusted under 35 U.S.C. 154(b) by 397 days.

(21) Appl. No.: 14/415,969

(22) PCT Filed: Feb. 20, 2014

(86) PCT No.: PCT/CN2014/072316
§ 371 (c)(1),
(2) Date: Jan. 20, 2015

(87) PCT Pub. No.: WO2015/120638
PCT Pub. Date: Aug. 20, 2015

(65) Prior Publication Data

US 2016/0360784 A1 Dec. 15, 2016

(30) Foreign Application Priority Data

Feb. 12, 2014 (CN) ..................... 2014 2 0063805 U

(51) Int. Cl.
*A24F 47/00* (2006.01)
*A61M 15/06* (2006.01)
(Continued)

(52) U.S. Cl.
CPC ......... *A24F 47/008* (2013.01); *H05B 1/0244* (2013.01); *H05B 3/04* (2013.01);
(Continued)

(58) Field of Classification Search
CPC ................................ A61M 15/06; A24F 47/00
See application file for complete search history.

(56) References Cited

U.S. PATENT DOCUMENTS

| | | | | |
|---|---|---|---|---|
| 6,196,218 B1 * | 3/2001 | Voges | A24F 47/002 128/200.14 |
| 2007/0074734 A1 * | 4/2007 | Braunshteyn | A24F 47/008 131/328 |
| 2013/0168880 A1 * | 7/2013 | Duke | A24F 47/008 261/78.2 |

FOREIGN PATENT DOCUMENTS

| | | |
|---|---|---|
| CN | 201064183 Y | 5/2008 |
| CN | 202774133 U | 3/2013 |

(Continued)

OTHER PUBLICATIONS

Machine Translation of CN 203194541 U. Original publication Sep. 18, 2013.*

(Continued)

*Primary Examiner* — Cynthia Szewczyk
(74) *Attorney, Agent, or Firm* — Ohlandt, Greeley, Ruggiero & Perle, LLP

(57) ABSTRACT

A battery rod assembly and an electronic cigarette are provided. The battery rod assembly includes a battery rod assembly body. The battery rod assembly body includes a suction end, a battery for supplying power to an atomizing assembly of the electronic cigarette and an aerosol passage communicating with the suction end. The battery and the aerosol passage are separated from each other inside the battery rod assembly body. Since the battery rod assembly body is provided with a separated and sealed aerosol passage, components inside the battery rod assembly may not be immersed by aerosol generated from atomization, thereby ensuring a long service life of the battery rod assembly. The
(Continued)

user is avoided from inhaling the cigarette liquid with the electronic cigarette including the battery rod assembly.

16 Claims, 9 Drawing Sheets

(51) Int. Cl.

| | |
|---|---|
| ***H05B 1/02*** | (2006.01) |
| ***H05B 3/04*** | (2006.01) |
| ***H05B 3/44*** | (2006.01) |

(52) U.S. Cl.
CPC ......... *H05B 3/44* (2013.01); *H05B 2203/014* (2013.01); *H05B 2203/021* (2013.01); *H05B 2203/022* (2013.01)

(56) References Cited

FOREIGN PATENT DOCUMENTS

| | | | |
|---|---|---|---|
| CN | 203194541 | U | 9/2013 |
| CN | 203692550 | U | 7/2014 |
| CN | 203692551 | U | 7/2014 |
| CN | 203723448 | U | 7/2014 |
| CN | 203723449 | U | 7/2014 |
| WO | 2013040193 | A2 | 3/2013 |

OTHER PUBLICATIONS

International Search Report dated Oct. 29, 2014 corresponding to PCT/CN2014/072316, 5 pp.
Written Opinion dated Oct. 29, 2014 corresponding to PCT/CN2014/072316, 3 pp.

* cited by examiner

BATTERY ROD ASSEMBLY AND ELECTRONIC CIGARETTE

CROSS REFERENCE TO RELATED APPLICATION

This application is the national phase of International Application No. PCT/CN2014/072316, titled "BATTERY ROD ASSEMBLY AND ELECTRONIC CIGARETTE", filed on Feb. 20, 2014, which claims the priority to Chinese Patent Application No. 201420063805.6, entitled "BATTERY ROD ASSEMBLY AND ELECTRONIC CIGARETTE", filed with the State Intellectual Property Office of People's Republic of China on Feb. 12, 2014, the entire disclosure of which is incorporated herein by reference.

TECHNICAL FIELD

The present application relates to the technical field of electronic cigarettes, and particularly to a battery rod assembly and an electronic cigarette.

BACKGROUND

A conventional electronic cigarette includes a battery rod assembly and an atomizing assembly, and the atomizing assembly is connected with the battery rod assembly at one end and connected with a suction nozzle at the other end. The atomizing assembly is provided with an aerosol passage in communication with the suction nozzle. The battery rod assembly is provided with a battery cartridge, a battery arranged inside the battery cartridge, and an airflow sensor for controlling the battery to supply power to the atomizing assembly. An airflow passage, which is in communication with the aerosol passage and is connected with the outer surface of the battery rod assembly, is formed between the battery cartridge and the battery. Once a suction performed by a user is sensed by the airflow sensor in the battery rod assembly, an electric heating wire assembly of the atomizing assembly is controlled to atomize the cigarette liquid in the atomizing assembly.

From the foregoing, there is no separate aerosol passage in the battery rod assembly. The aerosol generated from the cigarette liquid atomized by the electric heating wire assembly may easily flow into the airflow passage, electronic components inside the battery rod assembly may be immersed by the aerosol, and accordingly, the electronic components are damaged and the service life of the battery rod assembly is affected. In addition, since the suction nozzle of the conventional electronic cigarette is connected to the atomizing assembly, the cigarette liquid in the atomizing assembly is apt to be inhaled in.

SUMMARY

In view of this, the present application provides a battery rod assembly and an electronic cigarette, which have a long service life.

A battery rod assembly includes a battery rod assembly body.

The battery rod assembly body includes a suction end, a battery for supplying power to an atomizing assembly of an electronic cigarette, and an aerosol passage communicating with the suction end.

The battery and the aerosol passage are arranged inside the battery rod assembly body and are separated from each other.

In the battery rod assembly, the battery rod assembly body includes a connection structure for detachably connecting with the atomizing assembly. The connection structure is located on the battery rod assembly body at a position far away from the suction end.

In the battery rod assembly, the battery rod assembly body further includes:

an airflow sensor located near the suction end and for generating a pulse signal; and a microcontroller connected with the airflow sensor and the battery.

In the battery rod assembly, the battery rod assembly body further includes:

a button arranged on the battery rod assembly body and for receiving an operation instruction of a user; and a tact switch for controlling the battery to supply power to the atomizing assembly, where the tact switch is electrically connected to the button and the battery.

In the battery rod assembly, the battery rod assembly body further includes:

a battery cartridge sleeved on the battery;

a suction nozzle serving as the suction end, which is detachably connected with the battery cartridge;

a battery holder arranged inside the battery cartridge and for retaining the battery; and a battery electrode electrically connected to the battery and the atomizing assembly.

An electronic cigarette includes an electronic cigarette body.

The electronic cigarette body includes a suction end, a liquid container for containing a cigarette liquid, an atomizing assembly for atomizing the cigarette liquid, and any of the above described battery rod assemblies.

The liquid container is arranged at an end of the electronic cigarette body far away from the suction end.

In the electronic cigarette, the atomizing assembly is located between the battery rod assembly and the liquid container. The suction end is located at the outside of one end of the battery rod assembly, or is located in a central portion of the battery rod assembly, or is located on the battery rod assembly at a position far away from the atomizing assembly.

In the electronic cigarette, the liquid container is detachably connected with the atomizing assembly.

In the electronic cigarette, the atomizing assembly and the battery rod assembly body are coaxially arranged.

In the electronic cigarette, the atomizing assembly includes:

an electric heating wire assembly for atomizing the cigarette liquid; and a liquid-guiding mechanism for conveying the cigarette liquid within the liquid container to the electric heating wire assembly for atomization.

In the electronic cigarette, the electronic cigarette body further includes an air inlet communicating with the aerosol passage.

The air inlet is arranged on an outer wall of the atomizing assembly, or the air inlet is arranged at an abutment face of the atomizing assembly and the liquid container.

In the electronic cigarette, the liquid container is a transparent container.

In the electronic cigarette, the liquid container is a glass bottle.

The present application provides the battery rod assembly and the electronic cigarette. The battery rod assembly includes the battery rod assembly body. The battery rod assembly body includes the suction end, the battery for supplying power to the atomizing assembly of the electronic cigarette, and the aerosol passage communicating with the suction end. The battery and the aerosol passage are separated from each other inside the battery rod assembly body. Since the battery rod assembly body includes a separated and sealed aerosol passage, components inside the battery rod assembly may not be immersed by aerosol generated from cigarette liquid atomized by the atomizing assembly when the battery rod assembly and the atomizing assembly are coupled to form the electronic cigarette, thereby ensuring a long service life of the battery rod assembly. In addition, since the atomizing assembly is arranged at the end of the electronic cigarette far away from the suction end, the user is avoided from inhaling the cigarette liquid with the electronic cigarette including the battery rod assembly.

BRIEF DESCRIPTION OF THE DRAWINGS

For illustrating technical solutions in embodiments of the present application or conventional technologies more clearly, drawings to be used to describe the embodiments or the conventional technologies are briefly described hereinafter. Apparently, the drawings in the following description are only for some embodiments of the present application, other drawings may be obtained by those skilled in the art based on these drawings without any creative efforts.

DETAILED DESCRIPTION OF THE EMBODIMENTS

Figure 1:
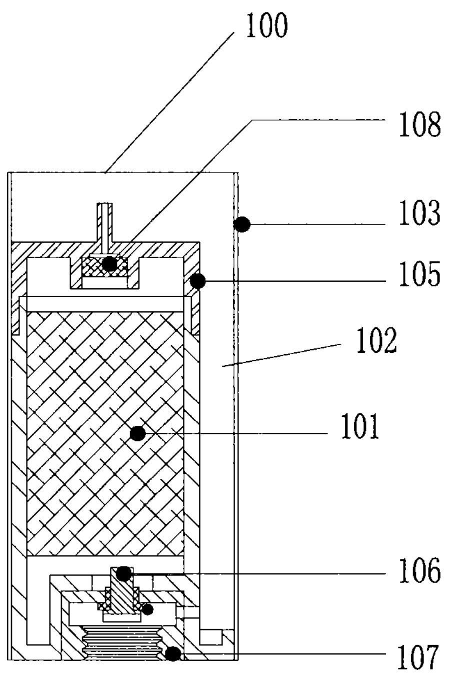
FIG. 1 is a schematic view showing an overall structure of a battery rod assembly according to a preferred embodiment of the present application.

The present application discloses a battery rod assembly, the structure of which is shown in FIG. 1.

As shown in FIG. 1, the battery rod assembly includes a battery rod assembly body. The battery rod assembly body is provided with a suction end 100, a battery 101 for supplying power to an atomizing assembly of an electronic cigarette, and an aerosol passage 102 in communication with the suction end 100 and separated from the battery 101.

The aerosol passage 102 provided in the battery rod assembly body is for the flow of atomized cigarette liquid, and a user may inhale, via the suction end 100, aerosol flowing through the aerosol passage 102.

Further, as shown in FIG. 1, the aerosol passage 102 arranged inside the battery rod assembly body may communicate the suction end 100 with an air inlet for conveying air into the electronic cigarette.

Preferably, the aerosol passage 102 is sealed inside the battery rod assembly body, i.e., the aerosol passage 102 is separated from other electronic components inside the battery rod assembly body.

With the battery rod assembly according to the embodiment, the atomized cigarette liquid flowing through the aerosol passage 102 may not corrode other electronic components in the battery rod assembly since the aerosol passage 102 is sealed inside the battery rod assembly body, and accordingly, the battery rod assembly has improved performance and a long service life.

The specific structure of the battery rod assembly is further described in detail below with reference to FIG. 1.

The battery rod assembly specifically includes a battery cartridge 103, a battery 101, a battery holder 105 and a battery electrode 106.

The suction end 100 shown in FIG. 1 may be formed with an extension of an end portion of the battery cartridge 103, and the suction end 100 and the battery cartridge 103 are formed integrally. Or, a suction nozzle serving as the suction end 100 is detachably connected to the battery cartridge 103. Specific configuration is not limited in the embodiment.

With the detachable suction nozzle in the embodiment, the user may replace or clean the suction nozzle at any time. Therefore, the cigarette liquid in the suction nozzle is avoided from being inhaled by the user, and the cigarette liquid in the battery rod assembly is easily cleared out.

The battery 101 is accommodated inside the battery cartridge 103.

The battery holder 105 for retaining the battery 101 is arranged inside the battery cartridge 103.

The battery electrode 106 is arranged at one end of the battery holder 105, and is electrically connected to the battery 101 and an atomizing assembly, where the atomizing assembly is arranged inside the electronic cigarette and is for atomizing the cigarette liquid.

A connection structure 107 for detachably connecting the battery rod assembly with the atomizing assembly is arranged in the battery rod assembly body. The connection structure 107 is located in the battery rod assembly body at a position far away from the suction end 100.

The battery rod assembly and the atomizing assembly are detachably connected via the connection structure 107. Specifically, the connection structure 107 may be a thread structure or a rotatable snap structure. The specific structure of the connection structure is not limited in the embodiment as long as a detachable connection of the battery rod assembly and the atomizing assembly may be achieved.

Applying the connection structure 107 is advantageous in that, it is convenient for the user to detach the atomizing assembly from the battery rod assembly at any time, and it is convenient for the user to replace the atomizing assembly or charge the battery rod assembly at any time.

Further, there are two configurations for the battery rod assembly in the application to control the atomizing assembly to atomize the cigarette liquid.

One configuration may be illustrated with reference to FIG. 1. In the battery cartridge 103, an airflow sensor 108 for generating a pulse signal is arranged at a position near the suction end 100.

When the airflow sensor 108 senses that the pressure in the aerosol passage 102 decreases, i.e., when the user sucks the electronic cigarette, the airflow sensor 108 generates the pulse signal.

In the embodiment, since the airflow sensor 108 is arranged near the suction end 100, the air flow sensor 108 has a high sensitivity in sensing suctions of the user. Therefore, the user may use the electronic cigarette more effectively.

A microcontroller for generating a control signal based on the pulse signal is provided and connected to the airflow sensor 108 and the battery 101. The microcontroller is connected to an electric heating wire assembly of the atomizing assembly, and the electric heating wire assembly atomizes the cigarette liquid based on the control signal.

With this configuration, tobacco cigarette smoking may be imitated, and the user may inhale the atomized cigarette liquid via the suction end 100.

Another configuration may be illustrated with reference to FIG. 2.

A button 201 for receiving an operation instruction from the user is arranged on the battery cartridge 103.

A tact switch 202 for generating a control signal based on the operation instruction is provided and is connected with the button 201.

The tact switch 202 is further for controlling the battery 101 to supply power to the atomizing assembly. The tact switch 202 is electrically connected to the button 201 and the battery 101.

With such a configuration, the user does not need to suck the suction end 100 to make the battery 101 to supply power to the atomizing assembly. Once the button 201 is pressed, the battery 101 may supply power to the atomizing assembly, the atomizing assembly atomizes the cigarette liquid, and accordingly, the user may inhale the aerosol.

Figure 2:
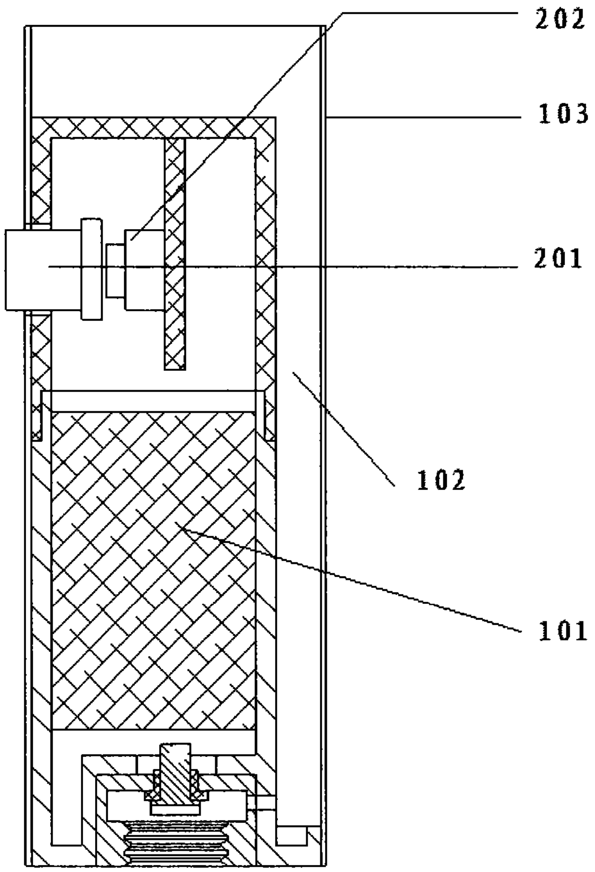
FIG. 2 is a schematic view showing an overall structure of a battery rod assembly according to a preferred embodiment of the present application.

The specific structure of the battery rod assembly provided in the present application is described in detail with the embodiments shown in FIGS. 1 to 2. The specific structure of an electronic cigarette including the battery rod assembly in the above embodiments is described in detail hereinafter in conjunction with an embodiment shown in FIG. 3.

Figure 3:
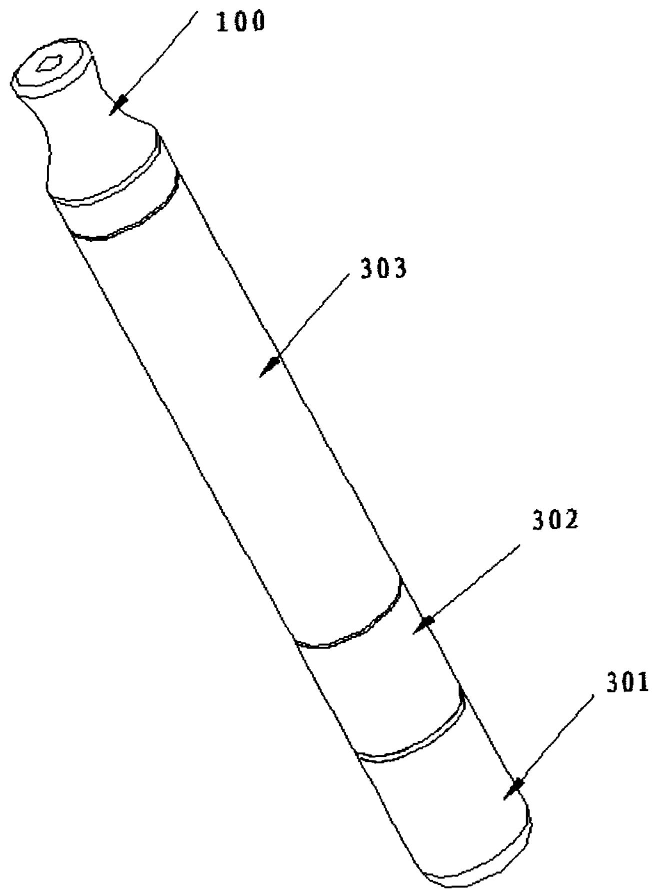
FIG. 3 is a schematic view showing an overall structure of an electronic cigarette according to a preferred embodiment of the present application.

An electronic cigarette shown in FIG. 3 includes an electronic cigarette body.

The electronic cigarette body includes a suction end 100, a liquid container 301 and an atomizing assembly 302.

The user may smoke through the suction end 100.

The liquid container 301 is configured to contain a cigarette liquid, i.e., an atomizable cigarette liquid is stored in the liquid container 301.

The atomizing assembly 302 is configured to atomize the cigarette liquid, i.e., the cigarette liquid within the liquid container 301 may be atomized by the atomizing assembly 302.

The electronic cigarette body further includes a battery rod assembly 303 for supplying power to the atomizing assembly 302.

The specific structure of the battery rod assembly 303 may be known with reference to the embodiments shown in FIGS. 1 to 2, which is not repeated here.

As shown in FIG. 3, the liquid container 301 is arranged at an end of the electronic cigarette body far away from the suction end 100. In this configuration, an aerosol passage inside the electronic cigarette body is not in communication with the liquid container 301 since the liquid container 301 is far away from the suction end 100, unatomized cigarette liquid in the liquid container 301 may not leak into the aerosol passage, and accordingly, the user may not inhale the unatomized cigarette liquid, thereby effectively avoiding the leakage of the cigarette liquid. In addition, since the aerosol passage is not in communication with the liquid container 301, the aerosol is avoided from condensing in the aerosol passage, and accordingly, the aerosol passage is effectively avoided from being blocked by condensed cigarette liquid.

The specific structure of the electronic cigarette according to the embodiment is further described in detail in conjunction with FIG. 3. The atomizing assembly 302 is located between the battery rod assembly 303 and the liquid container 301. The suction end 100 is located at the outside of one end of the battery rod assembly 303, or the suction end 100 is located in a central portion of the battery rod assembly 303, or the suction end 100 is located on the battery rod assembly 303 at a position far away from the atomizing assembly 302.

Specifically, for the suction end 100 located at the outside of one end of the battery rod assembly 303, the suction end 100 and the battery rod assembly 303 may be coaxially arranged. With this configuration, the electronic cigarette has an intuitive imitation of the appearance of a tobacco cigarette, and the overall aerosol passage is relatively straight, thereby effectively reducing accumulation of the cigarette liquid.

Alternatively, the suction end 100 is arranged in the central portion of the battery rod assembly 303, or the suction end 100 is located on the battery rod assembly 303 at a position far away from the atomizing assembly 302.

In the present application, the specific position of the suction end 100 is not limited.

In the embodiment, the atomizing assembly 302 and the battery rod assembly 303 are coaxially arranged, to provide the electronic cigarette with an overall structure similar to a tobacco cigarette, to be accordant with customary use of the user, and to reduce accumulation of the cigarette liquid.

Certainly, the specific configuration is not limited in the embodiment. For example, the battery rod assembly 303, the atomizing assembly 302 and the liquid container 301 which are connected successively may be arranged unevenly, and consequently, the overall appearance of the electronic cigarette may be irregular and the electronic cigarette may be in any irregular shape.

Alternatively, the atomizing assembly 302 and the battery rod assembly 303 may not be coaxially arranged. The liquid container 301 and the atomizing assembly 302 may be arranged parallel to each other, the liquid container 301 and the atomizing assembly 302 are respectively connected to the battery rod assembly 303, and the overall structure of the electronic cigarette is in a T-shape.

Therefore, the overall structure of the electronic cigarette is not limited in the embodiment as long as the liquid container 301 is arranged at a position far away from the suction end 100.

In the embodiment, the atomizing assembly 302 is located between the battery rod assembly 303 and the liquid container 301, and the atomizing assembly 302 is far away from the suction end 100. In using the electronic cigarette according to the embodiment, the user may not be scalded by the heat generated when the atomizing assembly 302 atomizes the cigarette liquid since the atomizing assembly 302 is far away from the mouth; hence, the security in using the electronic cigarette is effectively improved. In addition, the user generally holds the battery rod assembly 303 when using the electronic cigarette, rather than holds the heating atomizing assembly 302 as in conventional art. Therefore, the temperature of the tobacco cigarette is effectively imitated, and the user may not scald the hand when using the electronic cigarette according to the embodiment, thereby improving the user experience during smoking.

Preferably, the liquid container 301 is detachably connected with the atomizing assembly 302 and/or the atomizing assembly 302 is detachably connected with the battery rod assembly 303.

Specifically, the detachable connection between the liquid container 301 and the atomizing assembly 302 and/or the detachable connection between the atomizing assembly 302 and the battery rod assembly 303 may be a thread connection or an engagement connection, etc. The specific way of connection is not limited in the embodiment, as long as the liquid container 301 is detachably connected with the atomizing assembly 302 and/or the atomizing assembly 302 is detachably connected with the battery rod assembly 303.

Applying the above detachable connection is advantageous in that, it is convenient for the user to replace the atomizing assembly 302 at any time, and the user may detach the liquid container 301 at any time to conveniently add the cigarette liquid into the liquid container 301 or to replace the liquid container 301. The connection between the liquid container 301 and the atomizing assembly 302 and/or the connection between the atomizing assembly 302 and the battery rod assembly 303 may be non-detachable, which is not limited here.

The specific structure of the atomizing assembly of the electronic cigarette is described in detail below in conjunction with an embodiment shown in FIG. 4.

Figure 4:
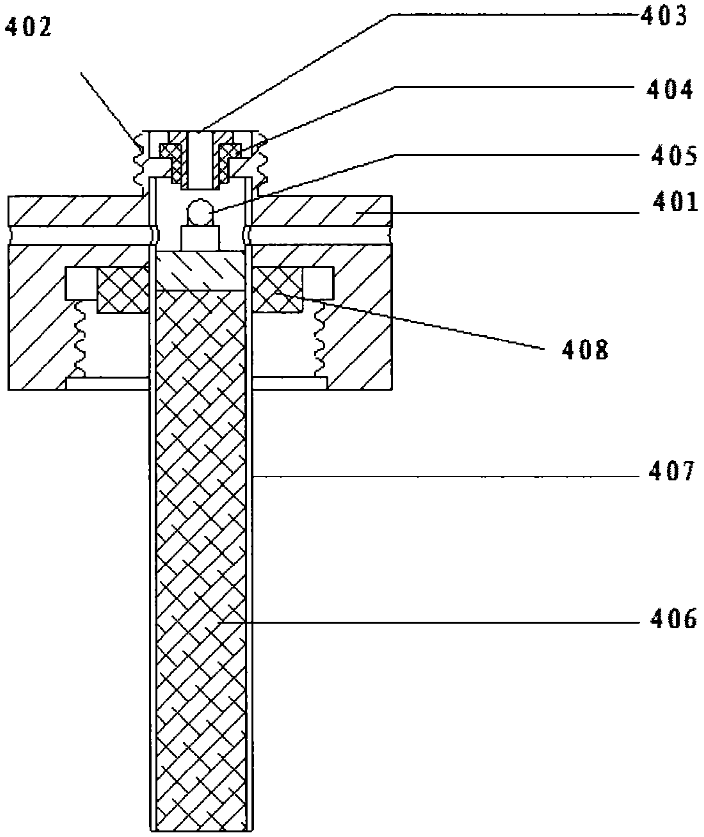
FIG. 4 is a schematic sectional view of an atomizing assembly of an electronic cigarette according to a preferred embodiment of the present application.

As shown in FIG. 4, the atomizing assembly 302 includes: an atomizer holder 401, a first threaded bushing 402, an atomizer electrode 403, an insulating ring 404, an electric heating wire assembly 405, a liquid-guiding mechanism 406 and an atomizer cartridge 407.

The first threaded bushing 402 is arranged on the top of the atomizer holder 401 and is detachably connected with the battery rod assembly 303.

In the embodiment, it is illustrated with an example that the atomizing assembly 302 and the battery rod assembly 303 are threadedly connected. The first threaded bushing 402 is arranged on the top of the atomizer holder 401 if the atomizing assembly 302 and the battery rod assembly 303 are to be threadedly connected. If other detachable connection structures are to be used, other connection structures may be arranged on the top of the atomizer holder 401, for example, an elastic strip is provided for an engagement connection. In the embodiment, the threaded bushing is only taken as an example, while the connection structure is not limited to the threaded bushing.

The atomizer electrode 403 is fixed inside the first threaded bushing 402.

The insulating ring 404 is arranged between the first threaded bushing 402 and the atomizer electrode 403.

The electric heating wire assembly 405 is electrically connected to the atomizer electrode 403, and the cigarette liquid may be atomized by the electric heating wire assembly 405.

The liquid-guiding mechanism 406 is for guiding the cigarette liquid within the liquid container 301 to the electric heating wire assembly 405 to be atomized. The liquid-guiding mechanism 406 may include liquid-guiding cotton, liquid-guiding fiber and so on, which is not limited here.

The atomizer cartridge 407 is arranged on the atomizer holder 401, and the liquid-guiding mechanism 406 is arranged in the atomizer cartridge 407.

Specifically, the atomizer cartridge 407 is inserted into the liquid container 301, and at least one liquid hole is arranged on the circumferential wall of the atomizer cartridge 407. The cigarette liquid within the liquid container 301 can be conveyed to the liquid-guiding mechanism 406 smoothly via the at least one liquid hole.

The specific structure of the liquid container according to the present application is detailed below in conjunction with an embodiment shown in FIG. 5.

Figure 5:
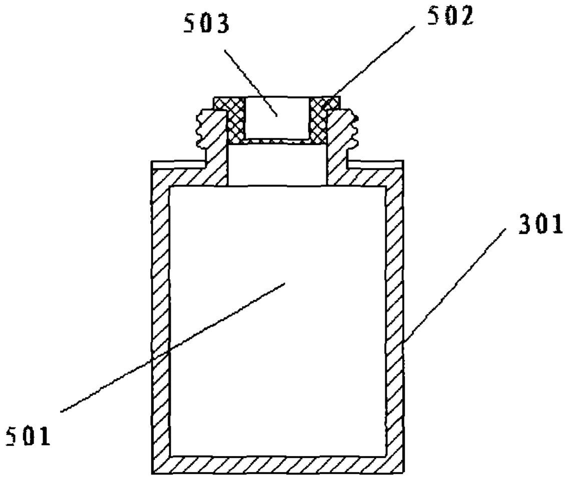
FIG. 5 is a schematic sectional view of a liquid container of an electronic cigarette according to a preferred embodiment of the present application.

As shown in FIG. 5, a sealed chamber 501 is arranged inside the liquid container 301. The cigarette liquid is sealedly stored in the sealed chamber 501.

To make the user acquire the amount of the cigarette liquid remained in the liquid container 301, the liquid container 301 is a transparent container. The user may acquire, at any time, the amount of the cigarette liquid remained in the electronic cigarette with the transparent liquid container 301, which facilitates the user in replacing the liquid container 301 in time.

Preferably, the liquid container 301 is a glass bottle. Since the property of glass is relatively stable, the smell of the cigarette liquid is avoided from being affected due to, for example, chemical reactions.

Preferably, an outer circumferential wall of the liquid container 301 made of glass is provided with calibrations. Hence, the user may estimate an available smoking duration with the remained cigarette liquid, which is convenient in using.

Preferably, a protective cartridge (not shown in the Figure) is sleeved on the liquid container 301, to protect the liquid container 301 made of glass from being broken due to falling off.

Preferably, the protective cartridge is provided with a cigarette liquid observation window for the user to observe the cigarette liquid.

For imitating the tobacco cigarette, the length of the electronic cigarette is generally same as that of the tobacco cigarette. For reducing a charging frequency and for ensuring a long service life of the battery rod assembly 303, the length of the battery rod assembly 303 may be equal to or longer than half of the whole length of the electronic cigarette. When the user uses the electronic cigarette according to the embodiment, he or she may naturally hold the electronic cigarette at an upper-middle portion of the electronic cigarette close to the suction end 100. The liquid container 301 may not be subjected to a holding force applied by the user since the liquid container 301 in the embodiment is arranged at an end far away from the suction end 100. Accordingly, the liquid container 301 outputs a relatively stable amount of the cigarette liquid to the atomizing assembly 302, thereby effectively ensuring a stable supply of aerosol and improving the user experience. Unstable amount of the aerosol, which is due to changing supplies of the cigarette liquid in response to changing forces applied at the end portion of the atomizing assembly by the user in the prior art, is avoided.

For sealing the liquid container 301 effectively and further avoiding the leakage of the cigarette liquid effectively, two arrangements are provided in the embodiment.

A first configuration is illustrated with reference to FIG. 4. For efficiently sealing the liquid container 301 connected to the atomizing assembly 302 and avoiding the leakage of the cigarette liquid in the liquid container 301, a sealing ring 408 for sealing the liquid container 301 is provided at a position where the atomizer holder 401 is connected with the liquid container 301.

The liquid container 301 can be sealed effectively by the sealing ring 408 arranged on the atomizer holder 401.

A second configuration is illustrated with reference to FIG. 5. An annular sealing plug 502 having a through hole is provided and sealedly coupled with an opening of the liquid container 301.

A piercable thin film 503 for sealing the liquid container 301 is arranged in the through hole of the annular sealing plug 502.

When inserting the atomizer cartridge 407 into the sealed chamber 501 of the liquid container 301, the atomizer cartridge 407 penetrates the piercable thin film 503. With the piercable thin film 503, the liquid container 301 with the atomizer cartridge 407 inserted therein still have a good sealing, thereby effectively avoiding the leakage of the cigarette liquid.

Since the liquid container 301 in the embodiment is provided with the annular sealing plug 502 having the pierable thin film 503, the liquid container 301 has a good sealing, which effectively avoids the leakage of the cigarette liquid and ensures a long service life of the electronic cigarette.

An aerosol passage 102, which is sealed and is configured to communicate the suction end 100 with an air inlet, is arranged inside the electronic cigarette of the present application.

Preferably, the aerosol passage 102 is sealed inside the battery rod assembly 303, i.e., the aerosol passage 102 is separated from other electronic components inside the battery rod assembly 303, which ensures the performance of the battery rod assembly and the service life of the electronic cigarette.

Specifically, the air inlet communicating with the aerosol passage 102 may be arranged in two ways. It should be known that the following arrangements of the air inlet are merely exemplary and are not for limitations, as long as the air inlet arranged in the electronic cigarette body can be communicated with the suction end 100 via the aerosol passage 102.

In a first arrangement, the air inlet may be arranged at an abutment face of the atomizing assembly 302 and the liquid container 301. Specifically, a protrusion or a rib may be arranged on the abutment face of the atomizing assembly 302 and the liquid container 301. Hence, an air inlet for entering of air is formed between the atomizing assembly 302 and the liquid container 301 which are threadedly connected with each other, and the air can flow into the aerosol passage 102 via the air inlet.

It should be noted that the way for arranging the air inlet is not limited, as long as an air inlet for entering of the air is formed between the atomizing assembly 302 and the liquid container 301.

Figure 6:
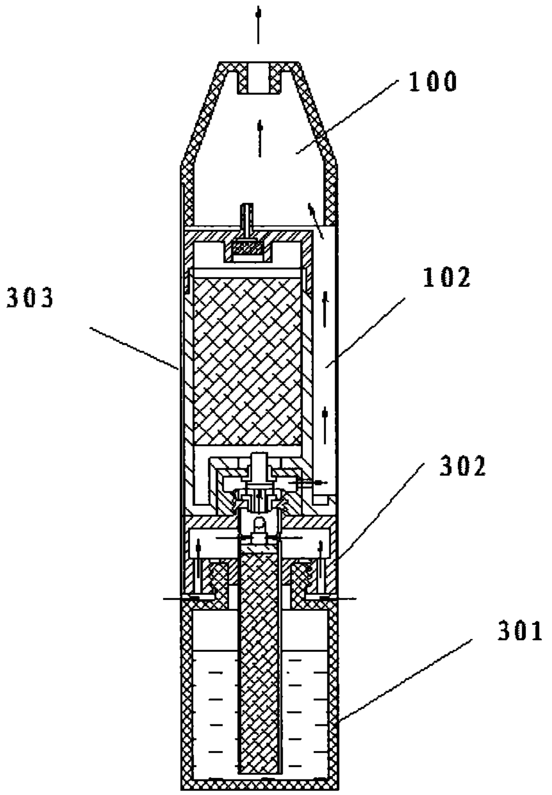
FIG. 6 is a schematic sectional view of an electronic cigarette according to a preferred embodiment of the present application.

The suction end 100 can be communicated with the air inlet via the aerosol passage 102. FIG. 6 is a schematic sectional view of an electronic cigarette having an air inlet arranged on the abutment face of the atomizing assembly 302 and the liquid container 301.

As shown in FIG. 6, the air inlet arranged on the abutment face of the atomizing assembly 302 and the liquid container 301 is communicated with the suction end 100 via the aerosol passage 102.

Specifically, the direction of the airflow in the electronic cigarette in the embodiment is indicated by arrows shown in FIG. 6. The airflow does not pass the liquid container 301. The aerosol atomized by the atomizing assembly 302 may flow to the suction end 100 without passing the liquid container 301; hence, the aerosol is avoided from condensing due to aerosol-absorbtion of the liquid container 301, and the aerosol passage 102 is further avoided from being blocked.

In a second arrangement, the air inlet may be arranged on an outer wall of the atomizing assembly 302, while the position and the number of the air inlet are not limited.

Figure 7:
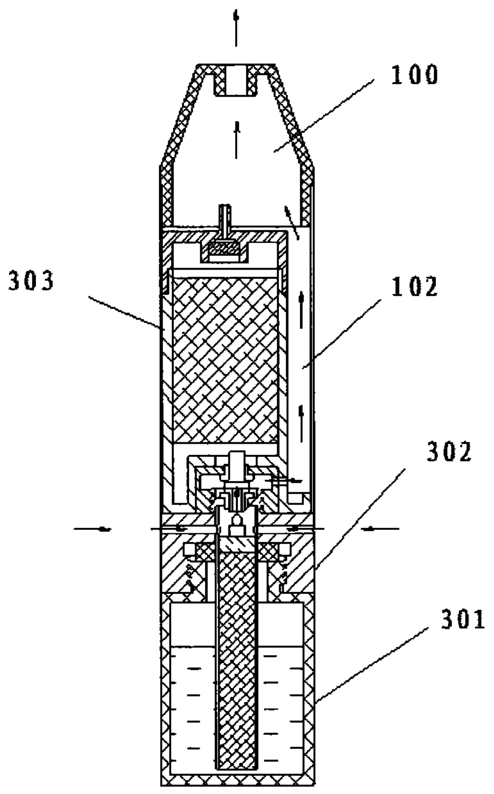
FIG. 7 is a schematic sectional view of an electronic cigarette according to a preferred embodiment of the present application.

The suction end 100 can be communicated with the air inlet via the aerosol passage 102. FIG. 7 is a schematic sectional view of an electronic cigarette having an air inlet arranged on the outer wall of the atomizing assembly 302.

As shown in FIG. 7, the air inlet, which is arranged on the outer wall of the atomizing assembly 302, is communicated with the suction end 100 via the aerosol passage 102.

Specifically, the direction of the airflow inside the electronic cigarette in the embodiment is indicated by arrows shown in FIG. 7. The airflow does not pass the liquid container 301. The aerosol atomized by the atomizing assembly 302 may flow to the suction end 100 without passing the liquid container 301; hence, the aerosol is avoided from condensing due to aerosol-absorbtion of the liquid container 301, and the aerosol passage 102 is further avoided from being blocked. A conventional situation that, the aerosol condenses when passing a liquid-containing region and the aerosol passage is blocked, is avoided.

An electronic cigarette according to an embodiment of the present application may have a light effect imitating a tobacco smoking effect. A specific structure is illustrated with reference to FIG. 8. The electronic cigarette shown in FIG. 8 includes a suction end 100 and a battery rod assembly 303, the specific structures of which can be known with reference to previous embodiments and are not repeated here.

In the embodiment, a liquid container 301 is integrated with an atomizing assembly 302, and the liquid container 301 is arranged at an end of the electronic cigarette body far away from the suction end 100.

Preferably, an aerosol passage 102 is arranged inside the liquid container 301, and an air inlet, which is in communication with the aerosol passage 102, is arranged at the bottom of the liquid container 301. The aerosol passage 102 extends to the suction end 100 and is in communication with the suction end 100.

Figure 8:
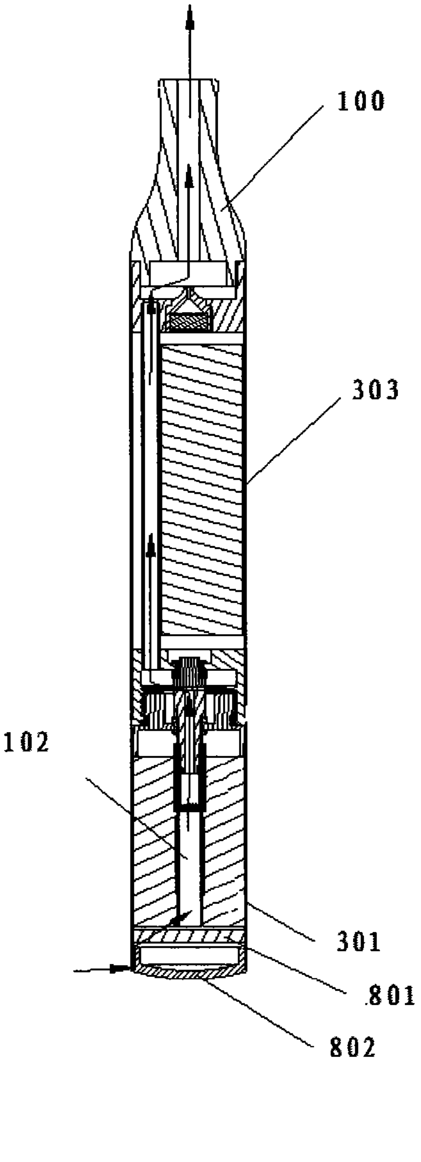
FIG. 8 is a schematic sectional view of an electronic cigarette according to a preferred embodiment of the present application.

The direction of airflow in the electronic cigarette is indicated by arrows shown in FIG. 8. As shown in FIG. 8, the aerosol passage 102 in the embodiment is longer than those in the previous embodiments. The temperature of the aerosol atomized by an electric heating wire assembly 8 may decrease due to the long aerosol passage 102, thereby ensuring the smoking experience of the user.

Preferably, a lighting module 801 may be arranged at the bottom of the electronic cigarette body. When the user sucks at the suction end 100, the lighting module 801 may emit light for imitating the burning of tobacco. Apparently, different light patterns can be set according to requirements of users to achieve different effects.

An end cap 802 for encasing the lighting module 801 is arranged at the bottom of the electronic cigarette body, and the end cap 802 may be transparent or opaque.

Figure 9:
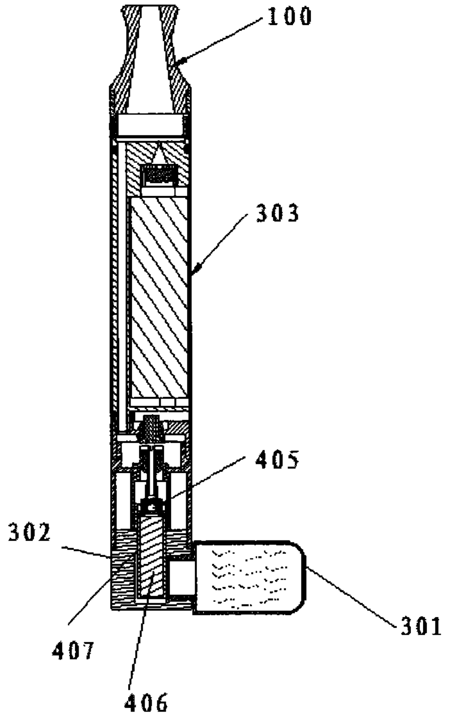
FIG. 9 is a schematic sectional view of an electronic cigarette according to a preferred embodiment of the present application.

To convey the cigarette liquid within the liquid container to the liquid-guiding mechanism more easily, an electronic cigarette having another structure is described in detail in conjunction with an embodiment shown in FIG. 9.

As shown in FIG. 9, the electronic cigarette includes a suction end 100 and a battery rod assembly 303, while the specific structures of which can be known with reference to the above embodiments and are not repeated here.

In the embodiment, a liquid container 301 for containing a cigarette liquid is arranged on an outer circumferential wall of an atomizing assembly 302, the cigarette liquid within the liquid container 301 is conveyed to a liquid-guiding mechanism 406 inside a atomizer cartridge 407 via a liquid hole arranged on the atomizer cartridge 407, and then the cigarette liquid is atomized by an electric heating wire assembly 405. The specific structure inside the atomizing assembly 302 can be known with reference to the above embodiments and is not limited in the embodiment.

In the embodiment, the flow direction of the cigarette liquid within the liquid container 301 is perpendicular to or angled to that of the cigarette liquid located in the atomizer cartridge 407 and conveyed to the electric heating wire assembly 405 to be atomized, to avoid the cigarette liquid from being overly conveyed to the atomizer due to vibration and so on. Thus, the cigarette liquid within the liquid container 301 can be conveyed to the liquid-guiding mechanism 406 inside the atomizer cartridge 407 stably, which ensures a stable amount of the aerosol. In addition, with this structure, the liquid container 301 made of glass may be avoided from being broken once the electronic cigarette falls off and the end portion of the electronic cigarette hits the ground.

In the embodiment, the liquid container 301 is threadedly connected to the atomizing assembly 302. Other ways such as an engagement connection may be alternatively used. The specific connection way is not limited in the embodiment.

It should be noted that, in the embodiment, the number and specific position of the liquid container 301 arranged on the side wall of the atomizing assembly 302 are not limited.

As shown in FIG. 9, if one liquid container 301 is arranged on the side wall of the atomizing assembly 302, the electronic cigarette body presents in an L-shape.

Figure 10:
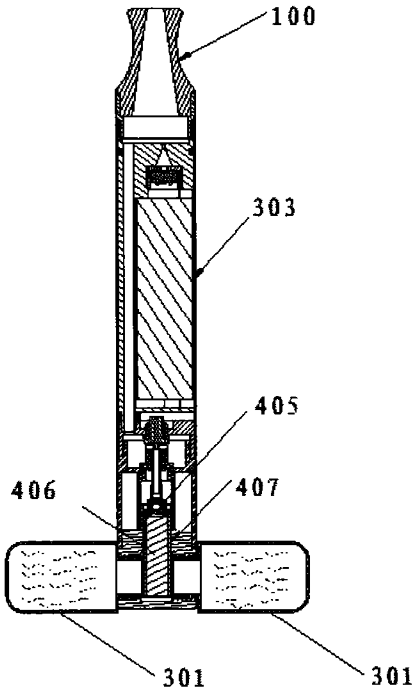
FIG. 10 is a schematic sectional view of an electronic cigarette according to a preferred embodiment of the present application.

Or, as shown in FIG. 10, if two liquid containers 301 are arranged on the side wall of the atomizing assembly 302 and the two liquid containers 301 are opposite to each other, the electronic cigarette body presents in a T-shape.

The technical solutions of the embodiments of the present application are described clearly and completely hereinabove in conjunction with the drawings of the embodiments of the present application. Apparently, the described embodiments are only a part of the embodiments of the present application, rather than all embodiments. All other embodiments made by those skilled in the art based on the embodiments in the present application without any creative labors fall into the protection scope of the present application.

The above embodiments are described in a progressive manner. Each of the embodiments is mainly focused on describing its differences from other embodiments, and references can be made among these embodiments for the same or similar portions.

Based on the above description of the disclosed embodiments, those skilled in the art are capable of carrying out or using the present application. It is obvious for those skilled in the art to make many modifications to these embodiments. The general principle defined herein may be applied to other embodiments without departing from the spirit or scope of the present application. Therefore, the present application is not limited to the embodiments disclosed herein, but should be defined by the broadest scope consistent with the principle and novel features disclosed herein.

The invention claimed is:

1. A battery rod assembly, comprising:
- a battery rod assembly body, wherein the battery rod assembly body comprises;
- a suction end,
- a battery configured to supply power to an atomizing assembly of an electronic cigarette,
- an aerosol passage communicating with the suction end, and
- an airflow sensor configured to generate a pulse signal and located at a position near the suction end and separated from the aerosol passage,
  - wherein the battery and the aerosol passage are arranged inside the battery rod assembly body and are separated from each other.

2. The battery rod assembly according to claim 1, wherein the battery rod assembly body is provided with a connection structure configured to detachably connect with the atomizing assembly, and the connection structure is located on the battery rod assembly body at a position far away from the suction end.

3. The battery rod assembly according to claim 2, wherein the battery rod assembly body further comprises:
- a microcontroller connected with the airflow sensor and the battery.

4. The battery rod assembly according to claim 2, wherein the battery rod assembly body further comprises:
- a button located on the battery rod assembly body and configured to receive an operation instruction of a user; and
- a tact switch configured to control the battery to supply power to the atomizing assembly, wherein the tact switch is electrically connected to the button and the battery.

5. The battery rod assembly according to claim 2, wherein the battery rod assembly body further comprises:
- a battery cartridge sleeved on the battery;
- a suction nozzle serving as the suction end, which is detachably connected with the battery cartridge;
- a battery holder arranged in the battery cartridge and configured to retain the battery; and
- a battery electrode electrically connected to the battery and the atomizing assembly.

6. The battery rod assembly according to claim 1, wherein the battery rod assembly body further comprises:
- a battery cartridge sleeved on the battery;
- a suction nozzle serving as the suction end, which is detachably connected with the battery cartridge;
- a battery holder arranged in the battery cartridge and configured to retain the battery; and
- a battery electrode electrically connected to the battery and the atomizing assembly.

7. An electronic cigarette, comprising:
- an electronic cigarette body, wherein the electronic cigarette body comprises a suction end, a liquid container configured to contain a cigarette liquid, an atomizing assembly configured to atomize the cigarette liquid, and a battery rod assembly;
- the battery rod assembly comprises a battery rod assembly body, wherein the battery rod assembly body comprises: a battery configured to supply power to the atomizing assembly of the electronic cigarette, and an aerosol passage communicating with the suction end, and the battery and the aerosol passage are arranged inside the battery rod assembly body and are separated from each other;
  - and an airflow sensor configured to generate a pulse signal and located at a position near the suction end and separated from the aerosol passage, and the liquid container is arranged at an end of the electronic cigarette body far away from the suction end.

8. The electronic cigarette according to claim 7, wherein the atomizing assembly is located between the battery rod assembly and the liquid container, and the suction end is located at the outside of one end of the battery rod assembly, or is located in a central portion of the battery rod assembly, or is located on the battery rod assembly at a position far away from the atomizing assembly.

9. The electronic cigarette according to claim 8, wherein the liquid container is detachably connected with the atomizing assembly.

10. The electronic cigarette according to claim 8, wherein the atomizing assembly and the battery rod assembly body are coaxially arranged.

11. The electronic cigarette according to claim 7, wherein the liquid container is detachably connected with the atomizing assembly.

12. The electronic cigarette according to claim 11, wherein the liquid container is a transparent container.

13. The electronic cigarette according to claim 12, wherein the liquid container is a glass bottle.

14. The electronic cigarette according to claim 7, wherein the atomizing assembly and the battery rod assembly body are coaxially arranged.

15. The electronic cigarette according to claim 14, wherein the atomizing assembly comprises:

an electric heating wire assembly configured to atomize the cigarette liquid; and a liquid-guiding mechanism configured to convey the cigarette liquid within the liquid container to the electric heating wire assembly for atomization.

16. The electronic cigarette according to claim 7, wherein the electronic cigarette body further comprises:

an air inlet communicating with the aerosol passage, the air inlet is arranged on an outer wall of the atomizing assembly, or the air inlet is arranged at an abutment face of the atomizing assembly and the liquid container.

* * * * *